(12) United States Patent
He et al.

(10) Patent No.: US 10,817,543 B2
(45) Date of Patent: Oct. 27, 2020

(54) METHOD FOR AUTOMATED SCALABLE CO-CLUSTERING (71) Applicant: NEC Laboratories Europe GmbH, Heidelberg (DE)

(72) Inventors: Xiao He, Heidelberg (DE); Luis Moreira-Matias, Heidelberg (DE)

(73) Assignee: NEC CORPORATION, Tokyo (JP)

( * ) Notice: Subject to any disclaimer, the term of this patent is extended or adjusted under 35 U.S.C. 154(b) by 256 days.

(21) Appl. No.: 16/029,723

(22) Filed: Jul. 9, 2018

(65) Prior Publication Data

US 2019/0251200 A1 Aug. 15, 2019

Related U.S. Application Data

(60) Provisional application No. 62/628,307, filed on Feb. 9, 2018.

(51) Int. Cl.
*G06F 16/00* (2019.01)
*G06F 16/28* (2019.01)
*G06F 16/2458* (2019.01)

(52) U.S. Cl.
CPC ........ *G06F 16/285* (2019.01); *G06F 16/2465* (2019.01)

(58) Field of Classification Search
CPC . G06F 16/2465; G06F 16/285; G06F 2216/03
USPC .................................................. 707/600–899
See application file for complete search history.

(56) References Cited

U.S. PATENT DOCUMENTS

| 8,996,350 | B1* | 3/2015 | Dub | G06F 16/35 |
| | | | | 704/1 |
| 2008/0071843 | A1* | 3/2008 | Papadimitriou | G06F 16/283 |
| 2008/0086493 | A1* | 4/2008 | Zhu | G06F 16/2462 |
| 2012/0005238 | A1* | 1/2012 | Jebara | G06Q 30/02 |
| | | | | 707/798 |
| 2014/0059423 | A1* | 2/2014 | Gorga | G06F 16/951 |
| | | | | 715/234 |

(Continued)

OTHER PUBLICATIONS

Ionnis Koutis, et al., "A nearly-m log n time solver for SDD linear systems", IEEE 52nd Annual Symposium on Foundations of Computer Science, Dec. 2011, pp. 590-598.

(Continued)

*Primary Examiner* — Michelle N Owyang
(74) *Attorney, Agent, or Firm* — Leydig, Voit & Mayer, Ltd.

(57) ABSTRACT

A method for processing an input data matrix so as to provide co-clustering assignments of rows and columns of the input data matrix includes generating, from the input data matrix, a graph of rows in the data matrix and a graph of columns in the data matrix, determining an objective function for generating a compact representation of the input data matrix, and generating the compact representation of the input data matrix by performing alternating optimization of the objective function until a test compact representation that causes the objective function to converge is generated. The method additionally includes generating a new graph of rows and a new graph of columns from the compact representation of the input data matrix, and returning a connected component of the new graph of rows and a connected component of the new graph of columns as the co-clustering assignments of the rows and columns.

16 Claims, 7 Drawing Sheets

(56) References Cited

U.S. PATENT DOCUMENTS

| | | | | |
|---|---|---|---|---|
| 2015/0317376 | A1* | 11/2015 | Bauer | G06F 16/285 |
| | | | | 707/737 |
| 2015/0347927 | A1* | 12/2015 | Zhang | G06N 5/022 |
| | | | | 706/12 |
| 2018/0024968 | A1* | 1/2018 | Clinchant | G06N 3/0454 |
| | | | | 706/12 |
| 2019/0362809 | A1* | 11/2019 | Okimoto | G06K 9/00127 |

OTHER PUBLICATIONS

Ioannis Koutis, et al., "Combinatorial Preconditioners and Multi-level Solvers for Problems in Computer Vision and Image Processing", Computer Vision and Image Understanding, vol. 115, issue 12, Dec. 2011, pp. 1638-1646.

Inderjit S. Dhillon, "Co-clustering documents and words using Bipartite Spectral Graph Partitioning", KDD '01 Proceedings of the seventh ACM SIGKDD international conference on Knowledge discovery and data mining, Aug. 26-29, 2001, pp. 269-274.

Sohil Atul Shah, et al., "Robust continuous clustering", PNAS, vol. 114, No. 37, Sep. 12, 2017, pp. 9814-9819.

* cited by examiner

METHOD FOR AUTOMATED SCALABLE CO-CLUSTERING

CROSS-REFERENCE TO PRIOR APPLICATION

Priority is claimed to U.S. Provisional Patent Application No. 62/628,307, filed on Feb. 9, 2018, the entire disclosure of which is hereby incorporated by reference herein.

FIELD

The present invention relates to computerized data processing, and more particularly, to computerized processing of data provided in the form of data matrices.

BACKGROUND

Clustering consists on grouping together objects (samples) giving their similar properties (features). However, in practical data mining problems, it is often observed that such groups actually share only a subset of such properties representing a context (e.g. peak hour definition in Transportation). The problem of modeling simultaneously groups of samples and features is known as bi-clustering or Co-Clustering (CoC). It outputs a natural interpretability of results through an explicit definition of a feature subspace for each resulting cluster. More technically, the co-clustering problem refers to simultaneously clustering the rows and columns of a data matrix.

Real-world applications of co-clustering extend across numerous different domains, from Biomedicine to Text mining and Marketing/Retail. An example of the latter is comprehensive customer segmentation. Traditional customer segmentation involves simple grouping (i.e. clustering) of customers in different segments according to their purchase history and the characteristics of their favorite items. In that example, each customer is assigned to one and one segment only (i.e. hard binding). Comprehensive customer segmentation elaborates on the previous example by removing this assumption. Here, each customer can be assigned to multiple segments depending on his preferences on different product categories. A 50-year old family woman can be a "regular purchaser" with respect to groceries and cosmetic products but a "seasonal" one for toys—which she buys in Christmas for her grandsons. A 20-year old male can be an occasional purchaser in general but with specific interests in action movies and books. A third example can be drawn from digital health, where co-clustering can be used to identify subgroups of patients with same mutations for a subset of genes for disease subtype discovery.

SUMMARY

In an embodiment, the present invention provides a method for processing an input data matrix so as to provide co-clustering assignments of rows and columns of the input data matrix. The method includes generating, from the input data matrix, a graph of rows in the data matrix and a graph of columns in the data matrix. Each node in the graph of rows is a row instance, each node in the graph of columns is a column instance, an edge is provided between two respective row instances if each of the two respective row instances is in the k-nearest neighborhood of the other, and an edge is provided between two respective column instances if each of the two respective column instances is in the k-nearest neighborhood of the other. The method additionally includes determining an objective function for generating a compact representation of the input data matrix. The objective function is constrained by the graph of the rows and the graph of the columns, and includes, for each of the graph of rows and the graph of columns, a regularization parameter, an auxiliary variable, and a non-convex function having a hyperparameter. The method further includes generating the compact representation of the input data matrix by performing alternating optimization of the objective function until a test compact representation that causes the objective function to converge is generated, generating a new graph of rows and a new graph of columns from the compact representation of the input data matrix, and returning a connected component of the new graph of rows as the co-clustering assignment of the rows and a connected component of the new graph of columns as the co-clustering assignment of the columns.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIG. 2b depicts an example of the input and output of the automatic scalable co-clustering method of FIG. 2a;

FIG. 4b depicts an example of the input and output of the automatic cancer subtype discovery pipeline depicted in FIG. 4a;

DETAILED DESCRIPTION

Existing solutions to the CoC problem typically suffer from at least one of the following issues: scalability, model/hyperparameter tuning, stability, and noise intolerance. Scalability concerns the ability to address largescale datasets while maintaining a reasonable ratio of run time to input size. Model/hyperparameter tuning refers to the impact that the choice of a number of clusters and/or other hyperparameter values has on the CoC process. The choice of hyperparameter values often requires human expertise and/or exhaustive and time consuming processes. Stability refers to the issue that clustering algorithms are not deterministic but instead depend on some sort of stochastic initialization that affects their output. Although there are well known heuristics to address this issue, they often require re-training a model multiple times. Noise intolerance refers to the ability of the CoC process to deal with noise. Real-world datasets often include noisy and incomplete records, and many clustering algorithms are not able to discern noise from valid patterns, especially when the ratio of noise to valid patterns increases in large-scale input data sets.

An ideal co-clustering process (i) can automatically generate clusters of rows and columns from an input data matrix without additional user inputs, and (ii) has linear runtime complexity with respect to the size of the input data matrix (i.e. the algorithm runtime is directly proportional to the size of the input data matrix). In contrast, state-of-the-art co-clustering methods require hyper-parameters provided by a user as input and have a quadratic or cubic time complexity. The traditional procedures to choose such hyper-parameters require intensive human labor and exhaustive search heuristics. Moreover, the high runtime complexity of the existing co-clustering algorithms prevents them from easily being used with large scale datasets (e.g. the purchase history of a client over multiple stores of a retail marketplace network).

Embodiments of the present invention provide improvements in the fields of big data and computerized data processing, among others, by providing robust continuous co-clustering processes that address one or more of the above described problems of the aforementioned state-of-the-art co-clustering processes. Embodiments of the present invention provide novel automated and scalable co-clustering methods and systems for performing such methods. Methods according to embodiments of the present invention provide co-clustering results having improved accuracy relative to existing state-of-the-art co-clustering methods. Specifically, embodiments of the present invention provide clusters of samples and clusters of features in which the similarity between individual samples and individual features is greater than in the clusters of samples and clusters of features generated by existing state-of-the-art co-clustering methods. Furthermore, the computational complexity of co-clustering methods according to embodiments of the present invention scales nearly linearly with respect to time regarding the size of an input data matrix (as compared to existing state-of-the-art co-clustering methods that scale quadratically or cubically with respect to time regarding the size of the input data matrix) and can therefore be used to perform co-clustering on larger data sets in a shorter amount of time than is possible with prior art co-clustering methods.

Embodiments of the present invention provide processes that include learning a graph-based two-sided representation of an input matrix, provide processes with an underlying optimization problem that is non-convex and therefore assures a flexible pool of solutions, provide co-clustering processes that have a near linear time complexity on the input size, and provide processes that can provide highly useful output despite limited user expertise. Contributions of co-clustering processes according to embodiments of the invention include the following. First, one or more embodiments of the invention provide co-clustering processes that utilize a generic non-convex optimization problem. Second, one or more embodiments of the invention provide co-clustering processes that have near-linear time complexity on the size of the input matrix. Third, one or more embodiments of the invention provide co-clustering processes that are able to find coclusters of arbitrary shape in a full non-parametric fashion, exhibiting low sensitivity to different hyperparameter values when empirically evaluated.

According to embodiments of the present invention, co-clustering processes include performing data preprocessing on an input data matrix. Such data preprocessing includes removing missing values and performing normalization. The co-clustering processes additionally include generating, from the preprocessed data matrix, a graph of the rows and a graph of the columns in the data matrix. Each node in the graph of rows is a row instance and each node in the graph of columns is a column instance. An edge between two row/column instances will exist if they are in the k-nearest neighborhood of one another. The co-clustering processes further generate a limited searching space/surface, i.e. an optimization surface, constrained by the graph of the rows and the graph of the columns to find a compact representation of the input data matrix. The compact representation of the input data matrix is another data matrix having the same size as the input data matrix but in which similar rows and similar columns are closer in distance as compared with the original input data matrix. The process uses a non-convex function to make the representation of connected row instances and column instances compact.

Next, the processes obtain a local optimal solution of the compact representation by solving an objective function, i.e. finding a compact representation that causes the objective function to converge. Specifically, in order to find the local optimal solution, the processes (i) initialize a test compact representation as being equal to the original input data matrix, (ii) determine the objective function, which utilizes the graph of rows and the graph of columns of original data matrix and which includes, for each of the graph of rows and the graph of columns, a regularization parameter and a non-convex function having a hyperparameter, (iii) provide a rewritten objective function by introducing, into the objective function for each of the graph of rows and the graph of columns, an auxiliary matrix variable, (iv) solve, by using a combinatory multigrid algorithm to solve a Sylvester equation, the rewritten objective function thereby providing an updated test compact representation, (v) update the auxiliary matrix variable for each of the graph of rows and the graph of columns, (vi) update the regularization parameter and the hyperparameter of the non-convex function for each of the graph of rows and the graph of columns, and (vii) iteratively performing (iv) through (vi) until an updated test compact representation is provided that causes the objective function to converge. As the iterative process for finding the local optimal solution is performed, the updating of the regularization parameter and the hyperparameter of the non-convex function for each of the graph of rows and the graph of columns can be performed less frequently than at every iteration. For example, updating the hyperparameter of the non-convex function and the regularization parameters can be performed every fourth iteration. In other words, at (vii), performing (iv) through (vi) can involve skipping (vi) during certain iterations. The processes then (viii) provide the updated test compact representation that causes the objective function to converge as the local optimal solution of the compact representation of the input data matrix.

The non-convex function is preferably a Geman-McClure function or the like. For instance, a Geman-McClure is a non-convex function on pairs of samples/features that are connected in a k-nearest neighbor graph. Non-convex functions are in general more robust on the noise edges than convex functions.

The Co-clustering processes according to embodiments of the invention further include discovering row clusters and column clusters on the local optimal solution of the compact representation of the input data matrix. Specifically, a K-nearest neighbor graph of rows and a K-nearest neighbor graph of columns are generated based on Euclidean distances in the local optimal solution of the compact representation of the input data matrix. Typically, these two K-nearest neighbor graphs are usually not fully connected, due to the compactness of the representation and the selection of a small number for K (e.g. 10). Samples/features inside the same connected component of the new graph of rows and the new graph of columns are then assigned to the same cluster. Further, all clusters are returned by processing all the connected components of the graphs. Finally, the process plots a heatmap for visualization by reordering the input data matrix according to the row and column clusters.

According to an embodiment, a method is provided for processing an input data matrix so as to provide co-clustering assignments of rows and columns of the input data matrix. The method includes generating, from the input data matrix, a graph of rows in the data matrix and a graph of columns in the data matrix. Each node in the graph of rows is a row instance, each node in the graph of columns is a column instance, an edge is provided between two respective row instances if each of the two respective row instances is in the k-nearest neighborhood of the other, and an edge is provided between two respective column instances if each of the two respective column instances is in the k-nearest neighborhood of the other. The method additionally includes determining an objective function for generating a compact representation of the input data matrix. The objective function is constrained by the graph of the rows and the graph of the columns, and includes, for each of the graph of rows and the graph of columns, a regularization parameter, an auxiliary variable, and a non-convex function having a hyperparameter. The method further includes generating the compact representation of the input data matrix by performing alternating optimization of the objective function until a test compact representation that causes the objective function to converge is generated, generating a new graph of rows and a new graph of columns from the compact representation of the input data matrix, and returning a connected component of the new graph of rows as the co-clustering assignment of the rows and a connected component of the new graph of columns as the co-clustering assignment of the columns. According to an embodiment, the non-convex function is a Geman-McClure function.

According to an embodiment, performing alternating optimization of the objective function until a test compact representation that causes the objective function to converge is generated includes (a) updating the regularization parameter and the hyperparameter of the non-convex function for each of the graph of rows and the graph of columns, (b) updating the auxiliary variable for each of the graph of rows and the graph of columns, (c) solving the objective function using at least one of the updated regularization parameter, the updated auxiliary variable, and the updated hyperparameter of the non-convex function for each of the graph of rows and the graph of columns thereby generating an updated test compact representation, and (d) determining whether the updated test compact representation causes the objective function to converge. According to an embodiment, if the updated test compact representation does not cause the objective function to converge, the method further includes repeating at least one of (a) and (b) and repeating (c) and (d). According to an embodiment, (b) updating the auxiliary variable for each of the graph of rows and the graph of columns is performed with greater frequency than (a) updating the regularization parameter and the hyperparameter of the non-convex function for each of the graph of rows and the graph of columns.

According to an embodiment, if the updated test compact representation causes the objective function to converge, the method further includes returning the updated test compact representation as the compact representation of the input data matrix.

According to an embodiment, solving the objective function includes solving a Sylvester equation. According to an embodiment, the Sylvester equation is solved by using a combinatorial multigrid algorithm. According to an embodiment, the combinatorial multigrid algorithm has a time complexity of $(O(m \log(m)))$ with respect to the size of the input data matrix.

According to an embodiment, updating the auxiliary variable for each of the graph of rows and the graph of columns is performed according to update rules. According to an embodiment, the update rules are derived by setting the partial derivative of the objective function regarding the auxiliary variables for each of the graph of rows and the graph of columns with a constant value for the compact representation equal to zero. According to an embodiment, graduated nonconvexity is used to update the hyperparameter of the non-convex function for each of the graph of rows and the graph of columns.

According to an embodiment, the method further includes initializing the test compact representation and, initializing, for each of the graph of rows and the graph of columns, the regularization parameter, the auxiliary variable, and the hyperparameter of the non-convex function. According to an embodiment, initializing the test compact representation includes setting the test compact representation equal to the input data matrix.

According to an embodiment, a non-transitory computer readable medium having stored thereon processor executable instructions that, when executed, cause a processor to perform a method for processing an input data matrix so as to provide co-clustering assignments of rows and columns of the input data matrix. The method includes generating, from the input data matrix, a graph of rows in the data matrix and a graph of columns in the data matrix. Each node in the graph of rows is a row instance, each node in the graph of columns is a column instance, an edge is provided between two respective row instances if each of the two respective row instances is in the k-nearest neighborhood of the other, and an edge is provided between two respective column instances if each of the two respective column instances is in the k-nearest neighborhood of the other. The method additionally includes determining an objective function for generating a compact representation of the input data matrix. The objective function is constrained by the graph of the rows and the graph of the columns, and includes, for each of the graph of rows and the graph of columns, a regularization parameter, an auxiliary variable, and a non-convex function having a hyperparameter. The method further includes generating the compact representation of the input data matrix by performing alternating optimization of the objective function until a test compact representation that causes the objective function to converge is generated, generating a new graph of rows and a new graph of columns from the compact representation of the input data matrix, and returning a connected component of the new graph of rows as the co-clustering assignment of the rows and a connected component of the new graph of columns as the co-clustering assignment of the columns. According to an embodiment, the non-convex function is a Geman-McClure function.

According to an embodiment of the invention, a system is provided for processing an input data matrix so as to provide co-clustering assignments of rows and columns of the input data matrix. The system includes a storing server configured to store an input data matrix and a computational server. The computational server is configured to generate, from the input data matrix, a graph of rows in the data matrix and a graph of columns in the data matrix, wherein each node in the graph of rows is a row instance and each node in the graph of columns is a column instance, wherein an edge is provided between two respective row instances if each of the two respective row instances is in the k-nearest neighborhood of the other, and wherein an edge is provided between two respective column instances if each of the two respective column instances is in the k-nearest neighborhood of the other. The computational server is further configured to determine an objective function for generating a compact representation of the input data matrix, wherein the objective function is constrained by the graph of the rows and the graph of the columns, and includes, for each of the graph of rows and the graph of columns, a regularization parameter, an auxiliary variable, and a non-convex function having a hyperparameter. The computational server is additionally configured to generate the compact representation of the input data matrix by performing alternating optimization of the objective function until a test compact representation that causes the objective function to converge is generated, generate a new graph of rows and a new graph of columns from the compact representation of the input data matrix, and return a connected component of the new graph of rows as the co-clustering assignment of the rows and a connected component of the new graph of columns as the co-clustering assignment of the columns. According to an embodiment, the non-convex function is a Geman-McClure function.

According to an embodiment of the invention for improving processing of data provided in the form of data matrices, a data matrix is received as input and clustering assignments for both samples and features represented in the input data matrix are provided as output. The clustering assignment can, for example, be used in customer segmentation to form clusters of customers and clusters of customer interests. Such a cluster of customers will include customers that share the same or similar customer interests, and such a cluster of customer interests will include customer interests that are shared by the same or similar customers. An input data matrix having p samples with f features each can be represented as $X=\{x_1, x_2, \ldots, x_p\} \in \mathbb{R}^{p \times f}$. The clustering assignments for samples can be represented as $C_p$ and the clustering assignments for features can be represented as features $C_f$.

In a first stage, a graph on the samples $G_p$ (i.e. a graph of rows) and a graph on the features $G_f$ (i.e. a graph of columns) are constructed. The graph construction can preferably be performed by providing a k-nearest neighbor graph. However kNN graphs can also be used. Each node in the graph of rows is a row instance and each node in the graph of columns is a column instance. In a k-nearest neighbor graph, there will be an edge between two row/column instances if one of the two row/column instances is a k-nearest neighbor of the other. In a kNN graph, there will be an edge between two row/column instances if both row/column instances are k-nearest neighbors of the other. Determining whether individual row/column instances are k-nearest neighbors involves computing the pairwise distances between each of the row/column instances. In general, the pairwise distances can be computed by calculating the distance between pairs of vectors provided by the input data matrix X. Each instance of a row in the input data matrix X and each instance of a column in the input data matrix X is a vector to represent samples/features. For example, in retail, a customer can be represented by a vector that has a value of 1 for each dimension that corresponds to a product that the customer purchases and that has a value of 0 for each dimension that corresponds to a product that the customer does not purchase. The pairwise distance in retail market segmentation could, e.g., be a measure of the similarity of the interests of two different customers, while the pairwise distance in gene expression data could, e.g., be a measure of the similarity of the genotype of two different patients. The edge sets of the graph on the samples $G_p$ and a graph on the features $G_f$ are denoted by $E_p$ and $E_f$.

In a second stage, a compact representation U of the input data matrix X that causes an objective function to converge is generated, or learned, via an iterative process in which the compact representation U and various parameters of the objective function are initialized and then updated until convergence of the objective function is achieved. The objective function uses the graph on the samples $G_p$ and the graph on the features $G_f$. Specifically, the compact representation U is generated by using the following objective function:

$$\min_U \|X - U\|_F^2 + \frac{\alpha}{2} \sum_{i,j \in E_P} \rho_p(\|u_i - u_j\|_2, \mu_p) + \quad (1)$$

$$\frac{\beta}{2} \sum_{i,j \in E_f} \rho_f(\|u^i - u^j\|_2, \mu_f)$$

Where F is the Frobenius norm, $\alpha$ and $\beta$ are regularization parameters, $\rho$ is the Geman-McClure function, $u_i$ and $u_j$ are the ith and jth rows of U, and $u^i$ and $u^j$ are the ith and jth columns of U. The Geman-McClure function is given by:

$$\rho(y, \mu) = \frac{\mu y^2}{\mu + y^2}, \quad (2)$$

where y is $\|u_i - u_j\|_2$ or $\|u^i - u^j\|_2$ from the above objective function and where $\mu$ is a hyperparameter that controls the convexity of the function. The above objective function ensures that the rows and columns of U are similar if they are neighbors, i.e. there is an edge between them, in the generated graph of rows $G_p$ and graph of columns $G_f$ respectively.

In order to determine a local optimum for the compact representation U, two auxiliary variables $L_p(i,j)$ for connections $(i,j) \in E_p$ and $L_f(i,j)$ for connections $(i,j) \in E_f$ are introduced, and the objective function is rewritten as:

$$\min_{U, L_p, L_f} \|X - U\|_F^2 + \frac{\alpha}{2} \sum_{i,j \in E_P} \left(L_P(i,j)\|u_i - u_j\|_2^2\right) + \quad (3)$$

$$\psi(L_P(i,j)) + \frac{\beta}{2} \sum_{i,j \in E_f} \left(L_f(i,j)\|u^i - u^j\|_2^2\right) + \psi(L_f(i,j)),$$

where $\psi(z) = \mu(\sqrt{z}-1)^2$. The rewritten objective function is biconvex on $(U, L_p)$ and $(U, L_f)$. When variable U is fixed, the optimal value of $L_p$ and $L_f$ can be derived in closed form. When variables $L_p$ and $L_f$ are fixed, solving the rewritten objective function amounts to solving a Sylvester equation. Therefore, alternating optimization can be used to determine the local optimum for the compact representation U by solving the rewritten objective function.

In order to solve the rewritten objective function using alternating optimization, setting the partial derivative of the rewritten objective function regarding $L_p$ and $L_f$ for constant U equal to zero provides update rules for $L_p$ and $L_f$:

$$L_p(i,j) = \left(\frac{\mu}{\mu + \|u_i + u_j\|_2^2}\right)^2 \quad (4)$$

$$L_f(i,j) = \left(\frac{\mu}{\mu + \|u^i + u^j\|_2^2}\right)^2.$$

Considering only $L_p$, and with $L_f$ fixed, the rewritten objective function can be expressed as:

$$\min_U \frac{1}{2}\|X - U\|_F^2 + \frac{\alpha}{2}\sum_{i,j \in E_p} L_p(i,j)\|U(e_i - e_j)\|_2^2, \quad (5)$$

where $e_i \in \mathbb{R}^n$ is an indicator vector with the ith element set to 1 and others set to 0. Taking the derivative of the above equation and setting it to zero, the solution equals the following linear least-squares problem:

$$AU = X, \text{ where } A = I + \alpha \sum_{i,j \in E_p} L_p(i,j)(e_i - e_j)(e_i - e_j)^T. \quad (6)$$

Similarly, with $L_p$ fixed, the rewritten objective function can be expressed as:

$$\min_U \frac{1}{2}\|X - U\|_F^2 + \frac{\alpha}{2}\sum_{i,j \in E_f} L_f(i,j)\|U(e_i - e_j)\|_2^2, \quad (7)$$

where $e_1 \in \mathbb{R}^n$ is an indicator vector with the ith element set to 1 and others set to 0. Taking the derivative of the above equation and setting it to zero, the solution equals the following linear least-squares problem:

$$UB = X, \text{ where } B = I + \beta \sum_{i,j \in E_f} L_f(i,j)(e_i - e_j)(e_i - e_j)^T. \quad (8)$$

When $L_p$ and $L_f$ are fixed, the rewritten objective function is a Sylvester equation, and therefore, the optimal U is equal to the solution of the following Sylvester equation:

$$AU + UB = 2X \quad (9).$$

Therefore, updating the compact representation U can be performed by updating $L_p$ and $L_f$ in an alternating fashion and solving the resulting Sylvester equation.

However, the Sylvester equation is in general expensive to solve. For example, the Bartels-Stewart algorithm is usually used to solve the general Sylvester Equation. However, the runtime complexity of the Bartels-Stewart algorithm is $O(p^3 + f^3)$, which prevents it to be used to solve large scale problem.

Alternatively, since A and B are sparse, the Sylvester equation can be solved using the Kronecker product and can be rewritten as:

$$C \cdot \text{vec}(U) = \text{vec}(X), \text{ where } C = A \otimes I_p + B \otimes I_f \quad (10),$$

where vec(U) and vec(X) are vectorized U and X, respectively, and where $\otimes$ indicates a Kronecker product. The above rewritten Sylvester equation is a linear least-squares problem on a sparse matrix C. A conjugate gradient method can be used to solve such a sparse linear system. A and B relate to the k-nearest neighbor graphs on the data with p samples and f features. Therefore, there are O(p) and O(f) non-zero entries in A and B respectively. Regarding C that is achieved by performing Kronecker product on A and an, there are O(pf) non-zero entries. The conjugate gradient method runs with complexity of $O(p^2 f^2)$, which is even worse compare to Bartels-Stewart algorithm with large p and f.

Nevertheless, embodiments of the present invention can solve the Sylvester equation with a near-linear method by taking advantages of certain properties of the Sylvester equation. Specifically, there is a critical property of the matrix C in the rewritten Sylvester equation: C is symmetric diagonally dominant (SDD). A matrix M is SDD if M is symmetric and:

$$M(i,i) \geq \sum_{i \neq j} |M(i,j)|. \quad (11)$$

The equality holds when M is a Laplacian matrix. With respect to the matrices A and B of the Sylvester equation, Let $N_{i,j} \in \mathbb{R}^{n \times n}$ and $N_{i,j} = (e_i - e_j)(e_i - e_j)^T$, thus $N_{i,j}$ is a Laplacian matrix. Therefore, $L_p(i,j)N_{i,j}$ is a Laplacian matrix as well, since $L_p(i,j) \geq 0$. The sum of Laplacian matrices is also a Laplacian matrix, thus $N = \sum_{i,j \in E_p} L_p(i,j)N_{i,j}$ is also a Laplacian matrix with $N(i,i) = \sum_{i \neq j} |N(i,j)|$. Therefore $A = I + \alpha N$ and $A(i,i) = \sum_{i \neq j} |A(i,j)| + 1$ is SDD. The same proof applies to B as well. Furthermore, a matrix $M \otimes I_p$ is SDD if $M \in \mathbb{R}^{n \times n}$ is SDD. Since both M and $I_p$ are symmetric, then:

$$M' = M \otimes I = I \otimes M = \begin{bmatrix} M & \cdots & 0 \\ \vdots & \ddots & \vdots \\ 0 & \cdots & M \end{bmatrix}. \quad (12)$$

$M(i,i) \geq \sum_{i \neq j} |M(i,j)|$, thus $M'(i,i) \geq \sum_{i \neq j} |M'(i,j)|$ and $M \otimes I_p$ is SDD. Therefore, matrix C of the rewritten Sylvester equation is also SDD. As a result of the matrix C being SDD, the rewritten Sylvester equation can be solved in near linear time (O(m log(m))), specifically through the use of a combinatorial multigrid algorithm with empirically linear runtime regarding pf. According to embodiments of the invention, the rewritten Sylvester equation can be solved according to the following combinatorial multigrid algorithm:

Input: C, x=vec(X) as in Eq. (10)

Output: u=vec(U) as in Eq. (10)

1. Generate a graph on C, there will be an edge between u, v if C(u,v)>0.

2. Get a set of vertices W={v} so that v satisfied:

$$\frac{\sum_u C(u,v)}{\max_u C(u,v)} > 4 \times \frac{1}{m} \sum_u \frac{\sum_u C(u,v)}{\max_u C(u,v)}$$

3. For each v ∋ W, remove all edges contributed by v, if the following equation is satisfied:

$$\sum_u C(u,v) < \frac{\sum_u C(u,v)}{\frac{1}{m}\sum_u \frac{\sum_u C(u,v)}{\max_u C(u,v)}}$$

4. Generate the partitions $V_1, V_2, \ldots$, for vertices in the same connected component of the graph.
5. R is a restriction matrix, where R(i,j)=1 if vertex i is in partition $V_j$
6. D=diag(C); A=D$^{-0.5}$AD$^{-0.5}$
7. z=(1−A)D$^{-0.5}$x+D$^{-0.5}$vec(X)
8. r=D$^{-0.5}$vec(X)−Az; w=R$^T$D$^{-0.5}$r
9. Q=R$^T$AR; Solve Qy=w
10. z=z+D$^{-0.5}$Ry
11. u=D$^{-0.5}$((I−A)z+D$^{-0.5}$b))z Graduated nonconvexity is used to update μ in the Geman-McClure function and to update α and β in the Sylvester equation by imposing the balance between data terms and pairwise terms. Thus the hyper-parameters are automatically learned. According to one or more embodiments of the invention, in determining a local optimum for the compact representation U of the input data matrix X, the compact representation is initialized so as to be equal to the input data matrix X, the auxiliary variables $L_p(i,j)$ and $L_f(i,j)$ are initialized so as to be equal to 1 for each edge (i,j) in the graphs $G_p$ and $G_f$, and the regularization parameters α and β are initialized according to the following initialization equations for the regularization parameters:

$$\alpha = \frac{\|X\|_2}{\|A-I\|_2} \qquad (13)$$
$$\beta = \frac{\|X\|_2}{\|B-I\|_2}$$

so that the data terms and pairwise terms in the objective function are balanced. Thereafter, a local optimum for the compact representation U is determined using the objective function by alternately updating $L_p$, $L_f$, and U until convergence of the above rewritten objective function (3) is achieved.

Graduated nonconvexity is used to update μ in the Geman-McClure function p. First, a locally convex approximation of the objective is obtained by setting a large enough μ. Thereafter, μ is automatically decreased every four iterations thereby gradually introducing nonconvexity into the objective function. Under certain assumptions, such continuation schemes are known to attain solutions that are close to the global optimum. After every update of μ, the regularization parameters α and β are automatically updated using the above initialization equations and the updated value of μ.

According to one or more embodiments of the invention, a robust continuous co-clustering process is performed using the following process (which, in steps 7 and 8, includes a third stage in which the clustering assignments for the samples $C_p$ and the clustering assignments for features $C_f$ are generated):

Algorithm 1: ROCCO
Input: Data Matrix X∈ℝ$^{p \times f}$.
Output: Co-cluster assignments $C_p$, $C_f$.
1. Construct mutual K-nearest neighbor graphs and their edge sets $E_p$ and $E_f$;
2. Provide objective function (1) and auxiliary variables, then rewrite objective function as (3);
3. Initialize $$U = X, L_p(i,j) = 1, L_f(i,j) = 1, \alpha = \frac{\|X\|_2}{\|A-I\|_2}, \beta = \frac{\|X\|_2}{\|B-I\|_2}$$

$\mu_p >> \max\|x_i - x_j\|_2^2, \mu_f >> \max\|x^i - x^j\|_2^2$;

4. While the rewritten objective function (3) does not converge:
 a. Update $L_p$ and $L_f$ using Eq. (4);
 b. Update A and B using Eq. (6) and (8);
 c. Update U by solving Eq. (10) using the above Combinatorial Multigrid Algorithm;
 d. Every four iterations, update $$\alpha = \frac{\|X\|_2}{\|A-I\|_2}, \beta = \frac{\|X\|_2}{\|B-I\|_2}, \mu_p = \frac{\mu_p}{2}, \mu_f = \frac{\mu_f}{2};$$

5. end
6. Construct mutual K-nearest neighbor graphs of rows and columns on U
7. Assign samples/features inside the same connected component to the same clusters and get clustering assignment $C_p$ and $C_f$
8. Return $C_p$, $C_f$ Embodiments of the present invention can be applied to retail customer segmentation. Market segmentation reveals divisions in a given market, where a market refers to a population of interest customers. A market segment is a subset of a market that is characterized by similar demands. Targeting different market segments is of great interest for retailers. Accurate market segmentation and automatic merchandising (e.g. providing discount vouchers and customized pricing) targeting different market segments is a key asset of modern marketing strategies.

Traditionally, markets are segmented by customers' geographic and demographic information. Then merchandising, e.g. generating discount vouchers, targeting all customers inside a given market segment—in either a manual or semi-automated fashion—can be performed using historical and typical sparse data (e.g. segments defined locally for a specific store or business segment). Nowadays, more and more marketers believe that behavioral market segmentation is superior to demographic and geographic market segmentation. A customer membership system can be used to build a database of customers' purchasing behavior and behavioral market segments can be obtained from such a database. Such data driven market segmentation methods are at the heart of modern marketing strategies.

Embodiments of the invention can be applied to improve behavioral market segmentation, e.g. to generate a behavioral market segment to which discount vouchers can be provided. The input to the system is: a group of customers, a list of items and the corresponding discounts that are given by the retailer. The output of the system is printed vouchers for all the customers.

Figure 1:
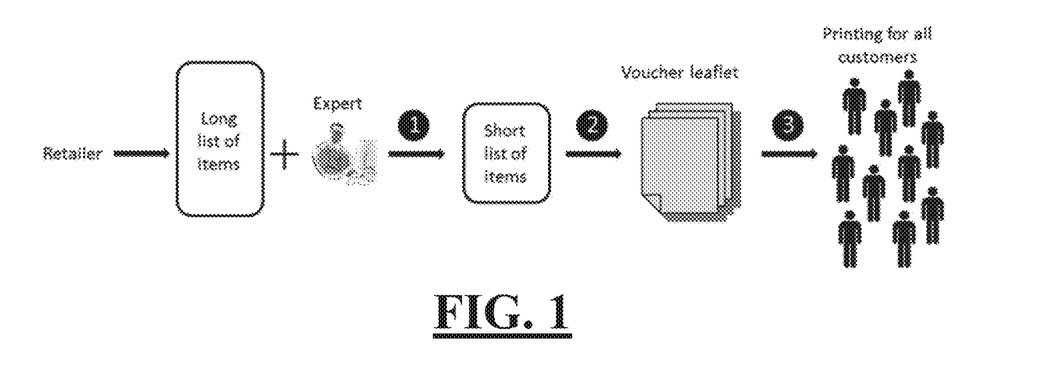
FIG. 1 provides an illustrative example of a traditional manual voucher printing system.

FIG. 1 depicts an illustrative example of a current State-of-the-art method for a voucher printing system. FIG. 1 provides an illustrative example of a traditional manual voucher printing system. Step 1—Manually reduce the number of items that will be with discount; Step 2—Grouping the items by their category and generate the single voucher leaflet; Step 3—Send the voucher to the printer and print it for all customers. The idea is to generate one single discount voucher for all the customers. They operate as follows: First, the input list of items that will be with discounts is manually reduced to a shorter list so that it covers a broad interest of all customers and it is not too long for printing. Secondly, the items are grouped by their categories and leaflet of voucher is automatically generated by the categories, e.g. one page shows one category. Finally, the discount voucher is sent to printer for printing. This voucher printing system depends on lots of manual work and expert knowledge. In addition, the single voucher leaflet cannot satisfy all the customers with different interests. If the voucher leaflet is too long, customers will get lost or lose interest to read it. If the voucher leaflet is too short, it cannot attract all customers' interests.

Figure 2A:
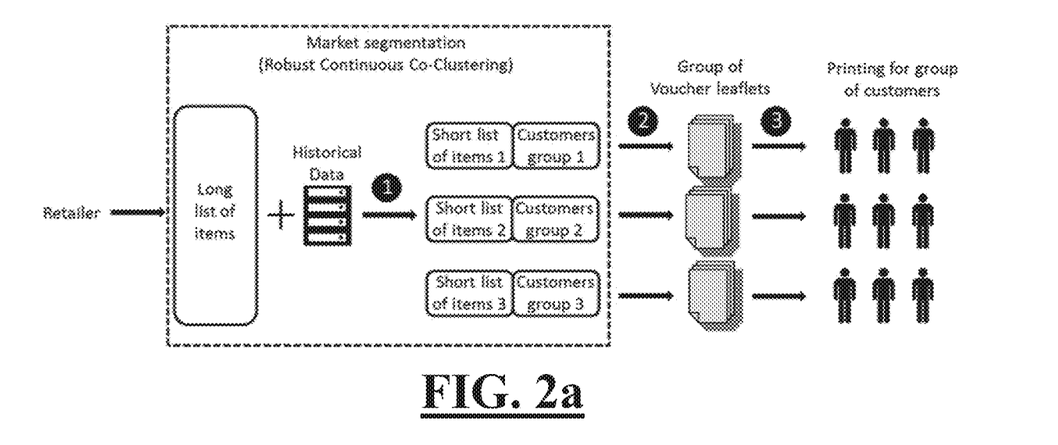
FIG. 2a provides an illustrative example of a novel voucher printing system according to an embodiment of the invention.
Figure 2B:
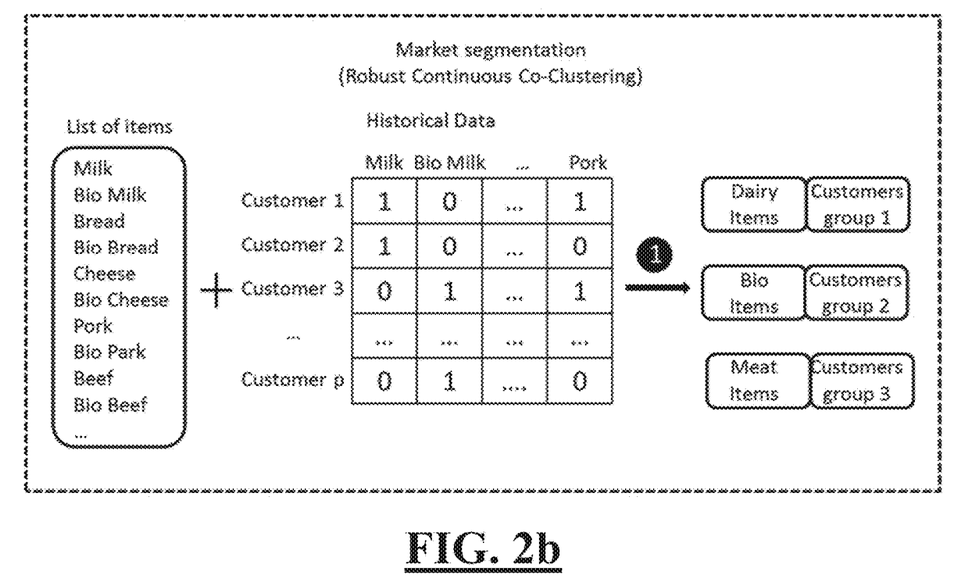
Figure 2C:
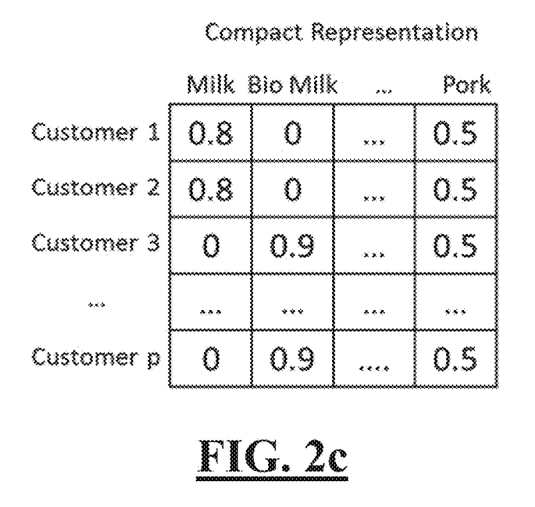
FIG. 2c depicts a compact representation of the historical data matrix of FIG. 2b.

Embodiments of the present invention can be applied to address such problems by replacing the manual filtering work by the automatic scalable co-clustering method in the voucher printing system as shown in FIG. 2a. FIG. 2a provides an illustrative example of a novel voucher printing system according to an embodiment of the invention. The dashed rectangles highlight a robust co-clustering process according to the embodiment of the invention. Step 1—Market segmentation tasks are being periodically (e.g. every week) issued on historical purchasing data to discovery market (group of customers) and its interest (group of items). For each market, short list of items with discount is automatically formed by taking those in both the long list and the discovered group of items; Step 2—For each market, grouping the items by their category and generate the voucher leaflet; Step 3—For each market, send the voucher to the printer and print it for customers of the market. FIG. 2b depicts an example of the input and output of the automatic scalable co-clustering method of FIG. 2a. In FIG. 2b, the input is lists of items and historical purchasing data. The output are customer groups and their targeted items. FIG. 2c depicts a compact representation of the historical data matrix of FIG. 2b.

Embodiments of the present application also have applications in cancer sub-type discovery. Many co-clustering methods have been used for cancer sub-type discovery in which gene expression data is partitioned into a checkerboard-like pattern that highlights the associations between groups of patients and groups of genes that distinguish those patients. By re-ordering the input matrix according to the clustering assignments, co-clustering results can be read by visualizing as a heatmap.

Figure 3:
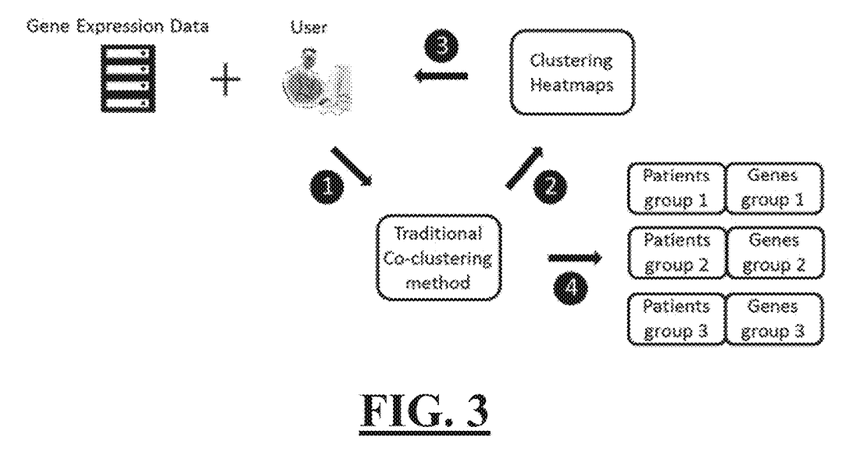
FIG. 3 provides an illustrative example of a traditional manual cancer subtype discovery pipeline.

A common way as shown in FIG. 3 is to perform cancer sub-type discovery from gene expression data is to try different hyper-parameters of co-clustering methods and then choose the one based on visual evaluation on heatmaps by the user. This method involves a lot of manual work and is subjective to the user. FIG. 3 provides an illustrative example of a traditional manual cancer subtype discovery pipeline. Step 1—The users manually choose the hyper-parameters for the traditional co-clustering method; Step 2—The traditional co-clustering method provides clustering results and generates heatmap; Step 3—The users evaluate heatmaps visually and choose the best results; Step 4—The users get the final clustering output with group of patients and genes. All 3 steps are iterated until satisfied results are achieved.

Figure 4A:
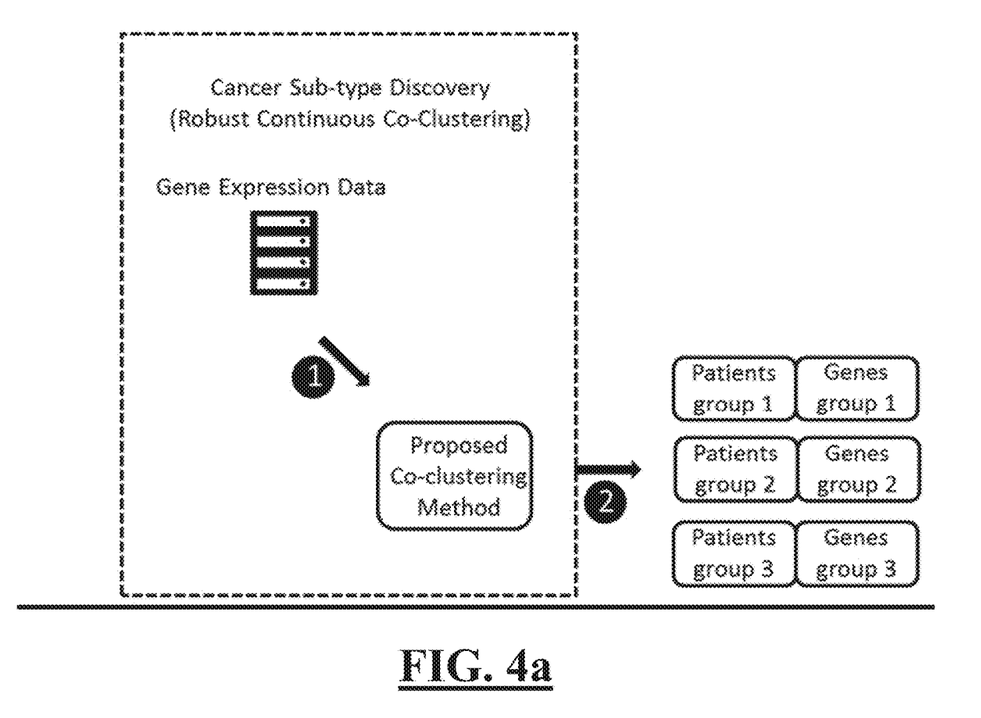
FIG. 4a provides an illustrative example of a proposed automatic cancer subtype discovery pipeline according to an embodiment of the invention.
Figure 4B:
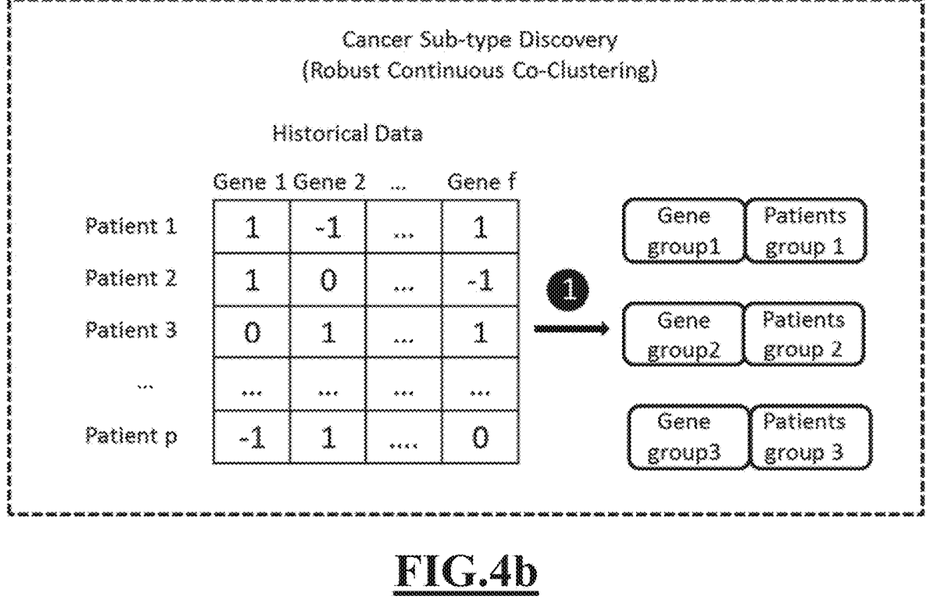
Figure 4C:
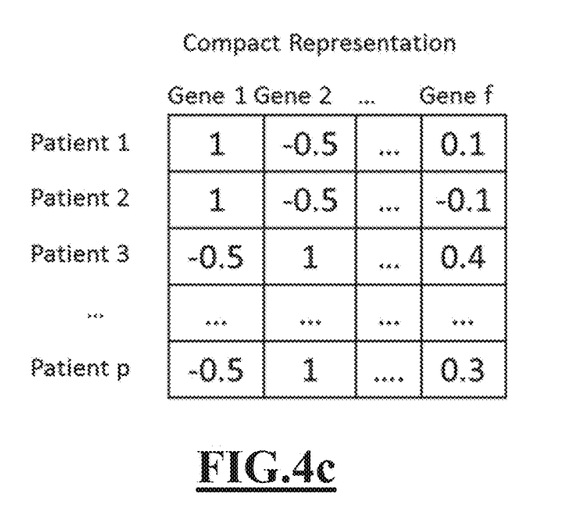
FIG. 4c depicts a compact representation of the historical data matrix of FIG. 4b.

Embodiments of the present invention can be applied for cancer subtype discovery so that the whole process can be automated and high quality co-clusters can be generated as shown in FIG. 4a. FIG. 4a provides an illustrative example of a proposed automatic cancer subtype discovery pipeline. Step 1—The raw data is sent to the proposed co-clustering method; Step 2—The proposed co-clustering method provides final clustering results of group of patients and genes. FIG. 4b depicts an example of the input and output of the automatic cancer subtype discovery pipeline depicted in FIG. 4a. The input includes the expression level (up or down) of genes for each patient. FIG. 4c depicts a compact representation of the historical data matrix of FIG. 4b.

Figure 5:
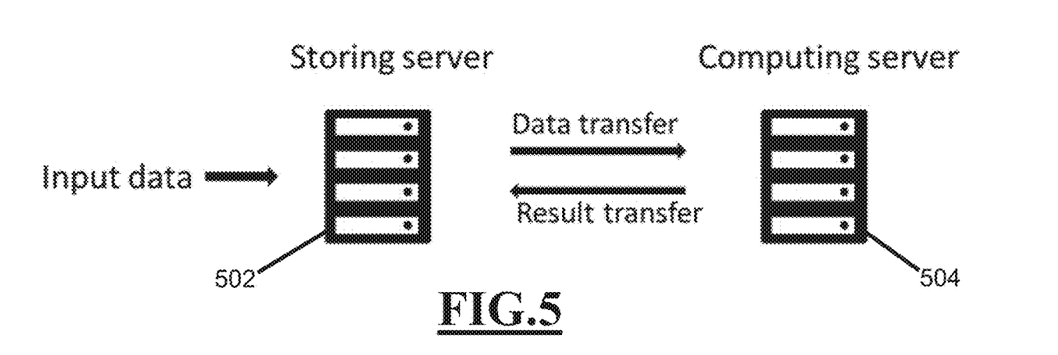
FIG. 5 depicts a system configured to perform a co-clustering process according to an embodiment of the invention.

FIG. 5 depicts a system configured to perform a co-clustering process according to an embodiment of the invention. The system includes a storing server 502 and a computational server 504. The storing server 502 is configured to store datasets and the outputs, e.g. the input data matrix X and the clustering assignments $C_p$ and $C_f$. The computational server 504 is configured to perform the various computations required to determine the clustering assignments $C_p$ and $C_f$ from the input data matrix X. Specifically, the computational server 504 is configured to (i) receive an input data matrix, (ii) construct a graph of rows and columns of the input data matrix, (iii) determine an objective function and generate a compact representation of the input data matrix that satisfies an objective function using the graphs constructed in (ii), (iv) construct graphs of rows and columns of the compact representation that satisfies the objective function, (v) assign rows and columns inside the same connected component of the graphs constructed in (iv) in order to generate clustering assignments, and (vi) return the clustering assignments. Each of the storing server 502 and the computational server 504 is a physical machine including compute resources, storage resources, and network resources. The compute resources at each server can include one or more processors each having one or more processor cores. The storage resources at each server can include computer readable memory, e.g., random-access-memory (RAM) and/or cache memory. The network resources include a physical network interface controller (NIC). Each server additionally includes a bus that couples various system components, e.g. the processors and the computer readable memory, together. The network interface controller of each server enables it to interface with other components, e.g. the other of the storing server 502 and the computational server 504.

Figure 6:
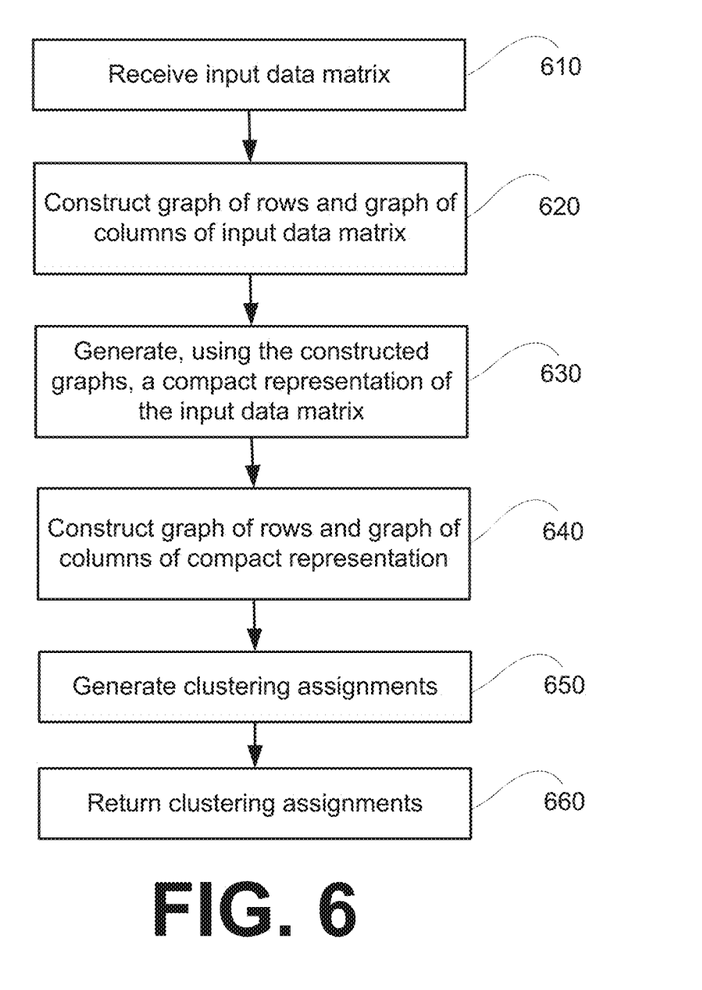
FIG. 6 depicts a process for performing a co-clustering process according to an embodiment of the invention.

FIG. 6 depicts a process for performing a co-clustering process according to an embodiment of the invention. The process depicts in FIG. 6 can be performed, for example, by the computational server 504. At 610, the process receives an input data matrix X At 620, the process constructs graphs of row instances and column instances of the input data matrix X At 630, the process generates, using the graphs constructed at 620, a compact representation U of the input data matrix X that satisfies an objective function. At 640, the process constructs graphs of row instances and column instances of the compact representation U. At 650, the process generates clustering assignments by assigning row instances and column instances inside the same connected component of the graphs constructed at 640 to the same clusters. At 660, the process returns the clustering assignments.

Figure 7:
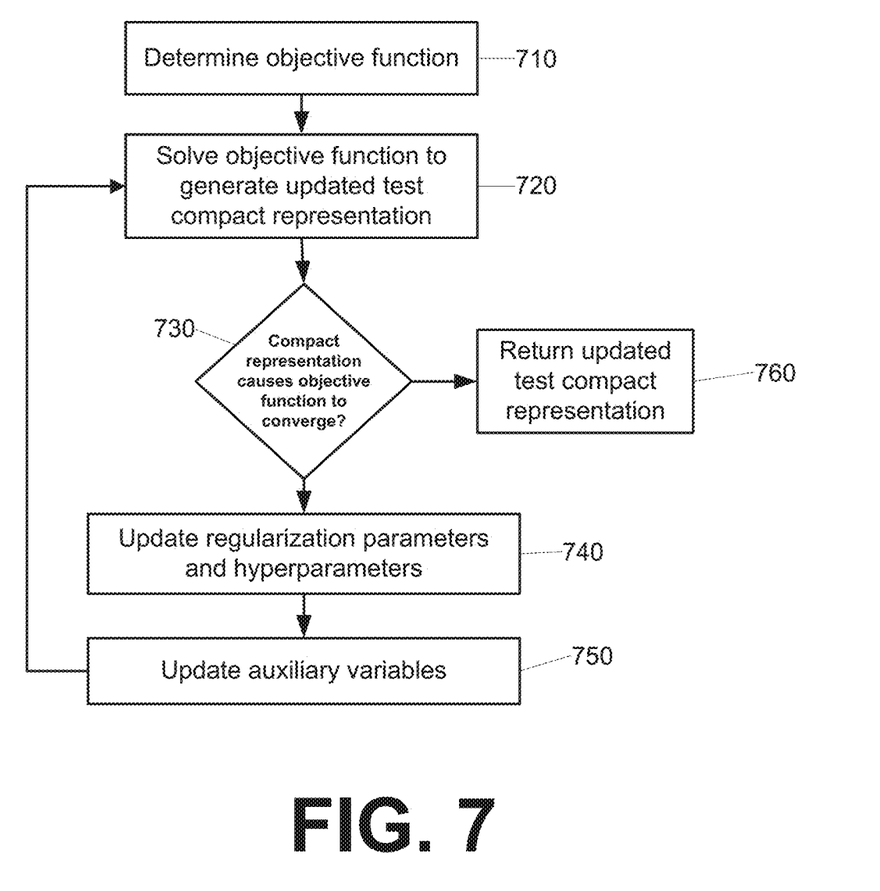
FIG. 7 depicts a process for generating a compact representation of an input data matrix that satisfies an objective function according to an embodiment of the invention.

FIG. 7 depicts a process for generating a compact representation of an input data matrix that satisfies an objective function according to an embodiment of the invention. At 710, the process determines an objective function that includes, for each of the graph of rows and the graph of columns, an auxiliary variable, a regularization parameter, and a Geman-McClure function having a hyperparameter and initializes a test compact representation, the auxiliary variables, the regularization parameters, and the hyperparameters. At 720, the process solves the objective function in order to generate an updated test compact representation. At 730, the process determines whether the updated test compact representation causes the objective function to converge. If the objective function does not converge, the process proceeds to 740 where regularization parameters and the hyperparameters are updated and then to 750 where the auxiliary variables are updated. Thereafter, the process returns to 720 and solves the objective function with the regularization parameters, hyperparameters, and auxiliary variables. If the objective function does converge, the process proceeds to 760 where it returns the updated test compact representation that causes the objective function to converge. According to variations of the embodiment depicted in FIG. 7, a counter can be employed ensure that step 740 is only performed for some multiple of iterations, e.g. every fourth iteration. In this manner, the auxiliary variables can be updated with a higher frequency than the regularization parameters and hyperparameters.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A method for processing an input data matrix so as to provide co-clustering assignments of rows and columns of the input data matrix, the method comprising:
    generating a compact representation of the input data matrix by performing an alternating optimization process, the alternating optimization process comprising:
        (i) specifying an objective function, the objective function being a function of a set of arguments that include a test matrix, a first auxiliary variable, and a second auxiliary variable,
        (ii) initializing the test matrix, the first auxiliary variable, and the second auxiliary variable,
        (iii) generating a graph of rows in the test matrix and a graph of columns in the test matrix, wherein each node in the graph of rows is a row instance and each node in the graph of columns is a column instance, wherein an edge is provided between two respective row instance nodes if each of the two respective row instance nodes is in the k-nearest neighborhood of the other, and wherein an edge is provided between two respective column instance nodes if each of the two respective column instance nodes is in the k-nearest neighborhood of the other,
        (iv) updating the first auxiliary variable according to an update rule for the first auxiliary variable to provide an updated first auxiliary variable, wherein the update rule for the first auxiliary variable is a function of a first set of arguments, values of the first set of arguments being determined from the graph of rows,
        (v) updating the second auxiliary variable according to an update rule for the second auxiliary variable to provide an updated second auxiliary variable, wherein the update rule for the second auxiliary variable is a function of a second set of arguments, values of the second set of arguments being determined from the graph of columns,
        (vi) updating the test matrix based on the updated first auxiliary variable and the updated second auxiliary variable, and
        (vii) providing the updated test matrix as the compact representation of the input matrix if the test matrix causes the objective function to converge, otherwise reinitializing the test matrix as the updated test matrix, the first auxiliary variable as the updated first auxiliary variable, and the second auxiliary variable as the updated second auxiliary variable and retuning to (iii);
    generating a new graph of rows and a new graph of columns from the compact representation of the input data matrix; and
    returning a connected component of the new graph of rows as the co-clustering assignment of the rows and a connected component of the new graph of columns as the co-clustering assignment of the columns.

2. The method according to claim 1, wherein the objective function includes, for each of the graph of rows and the graph of columns, a regularization parameter, an auxiliary variable, and a non-convex function having a hyperparameter, and
    wherein the alternating optimization process further includes:
    updating the regularization parameter and the hyperparameter of the non-convex function for each of the graph of rows and the graph of columns.

3. The method according to claim 2, wherein (b) the updating the first auxiliary variable and the updating the second auxiliary variable are performed with greater frequency than the updating the regularization parameter and the hyperparameter of the non-convex function for each of the graph of rows and the graph of columns.

4. The method according to claim 1, wherein the updating the test matrix based on the updated first auxiliary variable and the updated second auxiliary variable includes solving a Sylvester equation.

5. The method according to claim 4, wherein the Sylvester equation is solved by using a combinatorial multigrid algorithm.

6. The method according to claim 5, wherein the combinatorial multigrid algorithm has a time complexity of (O(m log(m))) with respect to the size of the input data matrix.

7. The method according to claim 1, wherein the update rule for the first auxiliary variable is derived by setting a partial derivative of the objective function with respect to the first auxiliary variable equal to zero, and wherein the update rule for the second auxiliary variable is derived by setting a partial derivative of the objective function with respect to the second auxiliary variable equal to zero.

8. The method according to claim 2, wherein graduated nonconvexity is used to update the hyperparameter of the non-convex function for each of the graph of rows and the graph of columns.

9. The method according to claim 1, wherein initializing the test matrix includes setting the test matrix equal to the input data matrix.

10. The method according to claim 2, wherein the non-convex function is a Geman-McClure function.

11. The method according to claim 1, wherein the input data matrix and the compact representation of the input data matrix have the same number of rows and the same number of columns.

12. The method according to claim 1, wherein the test matrix has the same number of rows and the same number of columns as the input data matrix and the compact representation of the input data matrix.

13. A non-transitory computer readable medium having stored thereon processor executable instructions, that when executed, cause a processor to perform a method for processing an input data matrix so as to provide co-clustering assignments of rows and columns of the input data matrix, the method comprising:
generating a compact representation of the input data matrix by performing an alternating optimization process, the alternating optimization process comprising:
(i) specifying an objective function, the objective function being a function of a set of arguments that include a test matrix, a first auxiliary variable, and a second auxiliary variable,
(ii) initializing the test matrix, the first auxiliary variable, and the second auxiliary variable,
(iii) generating a graph of rows in the test matrix and a graph of columns in the test matrix, wherein each node in the graph of rows is a row instance and each node in the graph of columns is a column instance, wherein an edge is provided between two respective row instance nodes if each of the two respective row instance nodes is in the k-nearest neighborhood of the other, and wherein an edge is provided between two respective column instance nodes if each of the two respective column instance nodes is in the k-nearest neighborhood of the other,
(iv) updating the first auxiliary variable according to an update rule for the first auxiliary variable to provide an updated first auxiliary variable, wherein the update rule for the first auxiliary variable is a function of a first set of arguments, values of the first set of arguments being determined from the graph of rows,
(v) updating the second auxiliary variable according to an update rule for the second auxiliary variable to provide an updated second auxiliary variable, wherein the update rule for the second auxiliary variable is a function of a second set of arguments, values of the second set of arguments being determined from the graph of columns,
(vi) updating the test matrix based on the updated first auxiliary variable and the updated second auxiliary variable, and
(vii) providing the updated test matrix as the compact representation of the input matrix if the test matrix causes the objective function to converge, otherwise reinitializing the test matrix as the updated test matrix, the first auxiliary variable as the updated first auxiliary variable, and the second auxiliary variable as the updated second auxiliary variable and retuning to (iii);
generating a new graph of rows and a new graph of columns from the compact representation of the input data matrix; and
returning a connected component of the new graph of rows as the co-clustering assignment of the rows and a connected component of the new graph of columns as the co-clustering assignment of the columns.

14. The non-transitory computer readable medium of claim 13, wherein the objective function includes, for each of the graph of rows and the graph of columns, a regularization parameter, an auxiliary variable, and a non-convex function having a hyperparameter, and
wherein the alternating optimization process further includes updating the regularization parameter and the hyperparameter of the non-convex function for each of the graph of rows and the graph of columns,
wherein the non-convex function is a Geman-McClure function.

15. A system for processing an input data matrix so as to provide co-clustering assignments of rows and columns of the input data matrix, the system comprising:
a storing server comprising a non-transitory computer readable medium, the storing server being configured to store an input data matrix; and
a computational server comprising one or more processors, the computational server being configured to:
generate a compact representation of the input data matrix by performing an alternating optimization process, the alternating optimization process comprising:
(i) specifying an objective function, the objective function being a function of a set of arguments that include a test matrix, a first auxiliary variable, and a second auxiliary variable,
(ii) initializing the test matrix, the first auxiliary variable, and the second auxiliary variable,
(iii) generating a graph of rows in the test matrix and a graph of columns in the test matrix, wherein each node in the graph of rows is a row instance and each node in the graph of columns is a column instance, wherein an edge is provided between two respective row instance nodes if each of the two respective row instance nodes is in the k-nearest neighborhood of the other, and wherein an edge is provided between two respective column instance nodes if each of the two respective column instance nodes is in the k-nearest neighborhood of the other, (iv) updating the first auxiliary variable according to an update rule for the first auxiliary variable to provide an updated first auxiliary variable, wherein the update rule for the first auxiliary variable is a function of a first set of arguments, values of the first set of arguments being determined from the graph of rows, (v) updating the second auxiliary variable according to an update rule for the second auxiliary variable to provide an updated second auxiliary variable, wherein the update rule for the second auxiliary variable is a function of a second set of arguments, values of the second set of arguments being determined from the graph of columns, (vi) updating the test matrix based on the updated first auxiliary variable and the updated second auxiliary variable, and (vii) providing the updated test matrix as the compact representation of the input matrix if the test matrix causes the objective function to converge, otherwise reinitializing the test matrix as the updated test matrix, the first auxiliary variable as the updated first auxiliary variable, and the second auxiliary variable as the updated second auxiliary variable and retuning to (iii);

generate a new graph of rows and a new graph of columns from the compact representation of the input data matrix; and return a connected component of the new graph of rows as the co-clustering assignment of the rows and a connected component of the new graph of columns as the co-clustering assignment of the columns.

16. The system according to claim 15, wherein the objective function includes, for each of the graph of rows and the graph of columns, a regularization parameter, an auxiliary variable, and a non-convex function having a hyperparameter, and wherein the alternating optimization process further includes updating the regularization parameter and the hyperparameter of the non-convex function for each of the graph of rows and the graph of columns, wherein the non-convex function is a Geman-McClure function.

* * * * *